United States Patent [19]

Fellman et al.

[11] Patent Number: 5,112,758
[45] Date of Patent: May 12, 1992

[54] TREATING BODY FLUIDS FOR DIAGNOSTIC TESTING

[75] Inventors: Jack H. Fellman; Andrew S. Goldstein, both of Portland, Oreg.

[73] Assignee: Epitope, Inc., Beaverton, Oreg.

[21] Appl. No.: 192,015

[22] Filed: May 9, 1988

[51] Int. Cl.$^5$ ............................................. G01N 31/00
[52] U.S. Cl. .......................................... 436/8; 436/17; 436/18; 436/63; 436/174; 436/176; 436/179
[58] Field of Search ................. 435/6, 188; 424/9, 95; 436/18, 174, 179, 176, 826, 8, 17, 63; 604/4, 48, 54

[56] References Cited

U.S. PATENT DOCUMENTS 3,887,703  6/1975  Manoussos et al. ................... 424/95
4,376,825  3/1983  Rubenstein et al. ................. 435/188

OTHER PUBLICATIONS

Ozawa et al.–Chem. Abst. vol. 104 (1986) p. 17605q.
Saeda et al.–Chem. Abst. vol. 101 (1984) p. 20136f.
Bonesvoll et al., Comparison between chlorhexidine and quaternary ammonium compounds w/regard to retention salivary conc'n, Arch. Oral Biol. 23(4), 1978, 289-294.
Yamada, correlation between viscosity & sialic acid content of human saliva, Nippon Shishubyo Gakkai Kaishi, 22(3), 366-76, 1980.

Primary Examiner—Sam Rosen
Attorney, Agent, or Firm—Wegner, Cantor, Mueller & Player

[57] ABSTRACT

A method of reducing the viscosity of a body fluid comprises mixing a body fluid with a cationic quaternary ammonium reagent. The body fluid is a mucopolysaccharide-containing body fluid which will be tested for a metabolite.

26 Claims, No Drawings

TREATING BODY FLUIDS FOR DIAGNOSTIC TESTING

This invention relates to the treatment of mucopolysaccharide-containing body fluids prior to testing for diagnostic purposes. In particular, this invention relates to the treatment of saliva prior to such testing.

Mucopolysaccharide-containing body fluids, such as saliva, contain antibodies and other metabolites that are useful in the diagnosis of diseases, including those of bacterial, viral, and metabolic origin. However, the viscous nature of such fluids, due to the nature of mucopolysaccharides, makes testing of these fluids difficult.

Saliva in particular presents problems as a diagnostic indicator. In order to prepare saliva for any laboratory testing procedure, the saliva must be rendered sufficiently fluid (i.e., viscosity must be reduced) and free from debris. Previously known techniques used to remove debris include centrifugation and filtration. However, no satisfactory method for reducing saliva viscosity resulting from mucopolysaccharides is currently available.

In addition to viscosity, the amount of saliva available can be a question. Individuals vary in their ability to produce sufficient quantities of saliva for testing purposes. Salivation is controlled by several factors, including time of day, emotional status, and whether certain drugs have been consumed. Techniques for inducing salivation include chewing on gum or wax, or placing a small, hard, round object under the tongue.

An objective of the present invention is to develop a satisfactory method for reducing the viscosity of mucopolysaccharide-containing body fluids, in particularly saliva, for diagnostic testing purposes. Another object of the present invention is to provide a practical test kit for collecting and reducing saliva viscosity, preferably including means for inducing saliva for collecting. Other objectives are apparent from the present specification and claims.

Accordingly, the present invention is a method of reducing the viscosity of a body fluid comprising mixing said body fluid with a cationic quaternary ammonium reagent. Also according to the present invention there is provided a kit for collecting a predetermined amount of a body fluid from a patient and reducing the viscosity thereof comprising a container for said body fluid having an indicium at a predetermined location denoting the fill level for said predetermined amount and containing a predetermined quantity of a cationic quaternary ammonium reagent therein sufficient to reduce the viscosity of said body fluid.

Viscosity reduction is caused by chemical interaction between the poly anionic mucopolysaccharides (comprising neuraminic acid and sulfated residues) with the cationic quaternary ammonium reagents. For example, electrostatic interaction between hexadecyltrimethylammonium chloride, a quaternary ammonium salt, and saliva mucopolysaccharides produces an insoluble aggregate. This results from the fact that long chain alkylquaternary ammonium detergents are soluble by nature of their highly hydrated chloride counter ion. When the hydrated chloride ion is displaced by the anionic mucopolysaccharide, the quaternary ammonium complex is rendered insoluble. Thus, many diverse quaternary ammonium compounds are useful in accordance with the present invention. Exemplary quaternary ammonium compounds have the formula

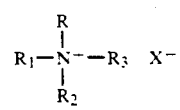

wherein R is a saturated or unsaturated, substituted or unsubstituted alkyl group having from about 4 to about 22 carbon atoms, a cycloaliphatic group having 5 to 6 carbon atoms, a polycyclic aliphatic group such as cis or trans decalin, or an alkyl substituted or unsubstituted aromatic group such as benzyl or phenyl; $R_1$, $R_2$, and $R_3$, which may be the same or different, are each a saturated or unsaturated alkyl group having from 1 to 4 carbon atoms, provided that one of $R_1$, $R_2$, and $R_3$ may be a saturated or unsaturated alkyl group having from about 4 to about 22 carbon atoms, a cycloaliphatic group having 5 to 6 carbon atoms, a polycyclic aliphatic group, or an aromatic group, or $R_1$, $R_2$, and $R_3$, together with the $N+$, may be formed of a 5 or 6 member heterocyclic group containing 1 or 2 nitrogen atoms, for example, a pyridine ring so as to form an alkyl pyridium chloride; and X is a halide, an acetate group, a sulfate group, or a phosphate group or other suitable organic or inorganic salts thereof. X is preferably chloride, bromide, or iodide. Examples of such compounds include hexadecyltrimethylammonium chloride (also known as trimethylhexadecylammonium chloride or "THAC"), benzylhexadecyldimethylammonium chloride, hexadecyltrimethylammonium stearate, cetyltrimethylammonium bromide or chloride, dioctadecyldimethylammonium chloride, cetylpyridinium chloride (or "CPC"), and ethylhexadecyldimethylammonium bromide. Preferable compounds of the above formula include hexadecyltrimethylammonium chloride and cetylpyridinium chloride.

Other useful quaternary ammonium compounds include resin beads or other supporting matrixes exhibiting a polycationic surface such as the cholestyramine resin Dowex-1. Dowex-1 is a synthetic, strongly basic anion exchange resin containing quaternary ammonium functional groups which are attached to a styrene-divinylbenzene copolymer. Its main constituent is polystyrene trimethylbenzylammonium and a $Cl^-$ anion, also containing divinylbenzene ($\approx 2\%$) and water ($\approx 43\%$). Cross linkage % is 1-10, and the typified structure of main polymeric groups is

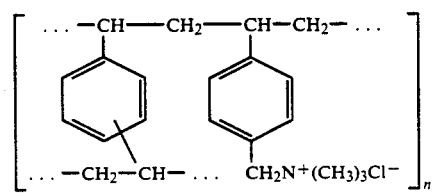

Further useful quaternary ammonium compounds include polymers of the formula

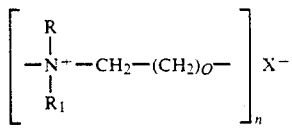

$$\left[ -\overset{R}{\underset{R_1}{N^+}} -CH_2-(CH_2)_O- \right]_n X^-$$

wherein R and $R_1$, which may be the same or different, are each an alkyl group having from 1 to 18 carbon atoms; n is at least 2; O is an integer from 1 to 18; and X is a halide, an acetate group, a sulfate group, or a phosphate group. Examples of such compounds include hexadimethrine bromide (available from Aldrich Chemical Co. under the name Polybrene ™).

Use of the quaternary ammonium compounds in accordance with the present invention has an added advantage in detecting antibodies in saliva. The excess quaternary ammonium detergent in the treated saliva, as it is exposed to the matrix-bound antigen, will electrostatically react with the anionic matrix, thus suppressing nonspecific binding of the other immune globulins in the saliva. This effect decreases background "noise," which can often otherwise be so great as to prevent useful detection of the specific binding of the antibody by the matrix bound antigens.

The amount of cationic quaternary ammonium reagent useful in accordance with the present invention is that amount sufficient to reduce the viscosity of the mucopolysaccharide-containing body fluid. Preferably, the final concentration of cationic quaternary reagent varies between about 0.05 and 5.0 g/100 ml of saliva. For example, the cationic quaternary ammonium reagent hexadecyltrimethylammonium chloride is preferably used in a range between about 0.005 and 0.05 ml/10 ml saliva, and cetylpyridinium chloride is preferably used in a range between about 0.05 and 0.5 g/10 ml saliva. Typically, desired use is one part reagent in 10 parts body fluid (e.g., 0.1 ml reagent plus 1.0 ml saliva). Using this scheme, the reagent concentration is prepared according to the reagent used. For example, "THAC" is preferably used at 0.1% to 0.01% (v/v). The final concentration in saliva is, therefore, 0.01% to 0.001%. "CPC" is preferably used at 1% to 0.1% (w/v) for a final concentration in saliva of 0.1% to 0.01%.

The test kit in accordance with the present invention comprises a container, such as a transparent tube or vial, having a mark indicating a predetermined volume, preferably 10 ml, for the amount of saliva to be added. The tube also contains the requisite amount of cationic quaternary ammonium reagent based on the saliva amount. Preferably, the test kit also comprises a salivation-inducing means for introduction into the patient's mouth. The salivation-inducing means is most preferably a "sour stick," i.e., a rod of plastic or other suitable rigid or semi-rigid material having attached at one end thereof a spongy material, such as a polyurethane sponge or cotton wool about 10-15 mm by 30-35 mm containing approximately 75 mg of ascorbic acid powder dusted on its surface. The sour stick is a disposable, single use device, which is packaged in a sealed polyethylene bag.

Optionally, a 1% iodine solution is useful as a germicide additive in conjunction with the present invention. Other useful germicides are disclosed in U.S. patent application Ser. No. 07/179,841 filed Apr. 11, 1988, in the name of Jack H. Fellman entitled "Germicidal Iodine Composition," which is incorporated in its entirety herein by reference. Other additives may be used, such as perfumes or other scents. (e.g., lemon scent which may also induce salivation), colorants, or the like.

Viscosity reduction in accordance with the present invention is useful in preparing mucopolysaccharide-containing body fluids for diagnostic testing, e.g., detecting antibodies against viruses such as HTLV-1, hepatitis, and herpes, proteins such as hormones, and small molecules such as glucose, amino acids, and amino acid derivatives.

The following non-limiting examples show the results of the method of the present invention. All parts and percentages are by weight unless indicated otherwise.

EXAMPLE 1

Saliva samples were collected from 100 individuals for further testing. In each case, a stick having a sponge tip of about ½ inch (12.7 mm)×1¼ inches (31.75 mm) dusted with about 75 mg of ascorbic acid was inserted under the individual's tongue to induce a copious amount of saliva. Ten ml of the saliva was collected in a test tube already containing 0.1 ml of a 0.01% (v/v) solution of trimethylhexadecylammonium chloride.

In a similar manner, saliva samples were collected from 20 individuals, but without any detergent.

EXAMPLE 2

The same procedure as in Example 1 was followed but using a 0.1 ml aliquot of a 0.1% (w/v) solution of cetylpyridinium chloride as the cationic detergent. Similar results were observed.

EXAMPLE 3

Saliva samples were collected and treated in accordance with the following procedure from 150 individuals who are seropositive for HIV antibody. Saliva is obtained by spitting into a 6 ounce, graduated, wide mouth cup. The saliva is mixed with one tenth its volume of quaternary (either CPC or THAC). The quaternary is prepared in water at the appropriate concentration. After 15 to 30 seconds, the mucopolysaccharides are precipitated and float at the top of the saliva sample. The liquid portion of the saliva is removed by mechanical pipettor and transferred to 4 ml testube. Note that extremely viscous saliva sample may require an additional aliquot of the quaternary. 100 µl of clarified saliva is mixed with 0.9 ml of PBS, pH 7.2 plus 0.03% Tween-20. This solution is placed in a tray containing an Epiblot strip and incubated one hour, room temperature. The strip is washed 3 times, 1 minute per wash with PBS/Tween. Peroxidase labeled goat anti-human antibody (at approximately 1 µg per ml) is added to the strip and incubated 30 minutes at room temperature. The strip is washed 3 times, 1 minute per wash with PBS/Tween. 1 ml of 0.3% 3, 3-diaminobenzidine plus 0.001% hydrogen peroxide is added to the strip for 5 minutes to develop the bands. The strip is washed with water and air dried. As a control, saliva samples were likewise collected and treated from 150 patients who are seronegative for HIV antibody.

All treated samples were tested for HIV antibody using Western Blot. Of the 150 seropositive individuals, all 150 were seropositive by Western Blot testing of the saliva samples treated in accordance with the present invention. The samples from all 150 controls showed seronegative results.

What is claimed is:

1. A method of testing a mucopolysaccharide-containing body fluid for the presence of a metabolite of interest, comprising reducing the viscosity of the mucopolysaccharide-containing body fluid by the sequential steps of collecting the fluid in a container and mixing said body fluid with a cationic quaternary ammonium reagent, and then testing the reduced viscosity fluid for the presence of the metabolite of interest in the body fluid.

2. A method as defined in claim 1, wherein said body fluid is saliva.

3. A method as defined in claim 1, wherein said cationic quaternary ammonium reagent is a cationic quaternary ammonium detergent.

4. A method as defined in claim 3, wherein a sufficient amount of said detergent is mixed with said body fluid to obtain a concentration of said detergent of from about 0.001 gram to about 0.1 gram per 100 ml of said body fluid.

5. A method as defined in claim 4, wherein said concentration of said detergent is from about 0.005 gram to about 0.01 gram per 100 ml of said body fluid.

6. A method as defined in claim 3, wherein said cationic quaternary ammonium detergent is represented by the formula:

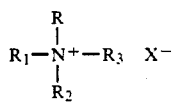

wherein

R is a saturated or unsaturated alkyl group having from about 4 to about 22 carbon atoms, a cycloaliphatic group having 5 to 6 carbon atoms, a polycyclic aliphatic group, or an aromatic group;

$R_1$, $R_2$, and $R_3$, which may be the same or different, are each a saturated or unsaturated alkyl group having from 1 to 4 carbon atoms, provided that one of $R_1$, $R_2$, and $R_3$ may be a saturated or unsaturated alkyl group having from about 4 to about 22 carbon atoms, a cycloaliphatic group having 5 to 6 carbon atoms, a polycyclic aliphatic group, or an aromatic group, or $R_1$, $R_2$, and $R_3$, together with the N+, may be formed of a 5 or 6 member heterocyclic group containing 1 to 2 nitrogen atoms; and X is a halide, an acetate group, a sulfate group, or a phosphate group.

7. A method as defined in claim 6, wherein said cationic quaternary ammonium detergent is hexadecyltrimethylammonium chloride.

8. A method as defined in claim 6, wherein said cationic quaternary ammonium detergent is cetylpyridinium chloride.

9. A method as defined in claim 1, wherein said cationic quaternary ammonium reagent is a supporting matrix having a polycationic quaternary ammonium surface.

10. A method as defined in claim 1, wherein said cationic quaternary ammonium reagent is a quaternary ammonium polymer represented by the formula:

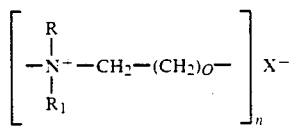

wherein

R and $R_1$, which may be the same or different, are each an alkyl group having from 1 to 18 carbon atoms;

n is at least 2;

O is an integer from 1 to 18; and

X is a halide, an acetate group, a sulfate group, or a phosphate group.

11. A method as defined in claim 1, further comprising a step of removing a sample of reduced viscosity body fluid from the container prior to testing.

12. A method as defined in claim 1, wherein the metabolite of interest is an antibody.

13. In a method of diagnosing a disease comprising testing a sample of a mucopolysaccharide-containing body fluid taken from a patient for the presence of a metabolite of interest, the improvement comprising reducing the viscosity of said sample of a body fluid by mixing a cationic quaternary ammonium reagent therewith prior to said testing, and then testing the reduced viscosity fluid for the presence of the metabolite of interest in the body fluid.

14. A method as defined in claim 13, wherein said cationic quaternary ammonium reagent is a cationic quaternary ammonium detergent.

15. A method as defined in claim 14, wherein a sufficient amount of said detergent is mixed with said body fluid to obtain a concentration of said detergent of from about 0.05 gram to about 5.0 gram per 100 ml of said body fluid.

16. A method as defined in claim 14, wherein said concentration of said detergent in said body fluid is between about 0.001 and 0.01% (v/v).

17. A method as defined in claim 14, wherein said cationic quaternary ammonium detergent is represented by the formula:

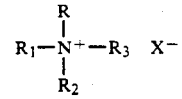

wherein R is a saturated or unsaturated alkyl group having from about 4 to about 22 carbon atoms, a cycloaliphatic group having 5 to 6 carbon atoms, a polycyclic aliphatic group, or an aromatic group;

$R_1$, $R_2$, and $R_3$, which may be the same or different, are each a saturated or unsaturated alkyl group having from 1 to 4 carbon atoms, provided that one of $R_1$, $R_2$, and $R_3$ may be a saturated or unsaturated alkyl group having from about 4 to about 22 carbon atoms, a cycloaliphatic group having 5 to 6 carbon atoms, a polycyclic aliphatic group, or an aromatic group, or $R_1$, $R_2$, and $R_3$, together with the N+, may be formed of a 5 or 6 member heterocyclic group containing 1 or 2 nitrogen atoms; and X is a halide, an acetate group, a sulfate group, or a phosphate group.

18. A method as defined in claim 17, wherein said cationic quaternary ammonium detergent is hexadecyltrimethylammonium chloride.

19. A method as defined in claim 17, wherein said cationic quaternary ammonium detergent is cetylpyridinium chloride.

20. A method as defined in claim 13, wherein said cationic quaternary ammonium reagent is a supporting matrix having a polycationic quaternary ammonium surface.

21. A method as defined in claim 13, wherein said body fluid is saliva.

22. A method as defined in claim 21, further comprising the steps of inducing salivation in said patient by introducing a non-toxic acidic substance to the patient's mouth and collecting the saliva thus induced in a container prior to reducing the viscosity thereof.

23. A method as defined in claim 22, wherein said acidic substance is citric acid.

24. A method as defined in claim 23, wherein said citric acid is coated on a substrate which is introduced into the patient's mouth.

25. A method as defined in claim 22, wherein said cationic quaternary ammonium reagent is contained in said container.

26. A method as defined in claim 13, wherein the metabolite of interest is an antibody.

* * * * *